(12) United States Patent
Esposito et al.

(10) Patent No.: US 7,892,253 B2
(45) Date of Patent: Feb. 22, 2011

(54) TOURNIQUET AND METHOD OF USE

(75) Inventors: Mark Esposito, Golden, CO (US); Jonathan Bennett, Fort Mill, SC (US)

(73) Assignee: Phil Durango, LLC, Golden, CO (US)

( * ) Notice: Subject to any disclaimer, the term of this patent is extended or adjusted under 35 U.S.C. 154(b) by 376 days.

(21) Appl. No.: 11/846,382

(22) Filed: Aug. 28, 2007

(65) Prior Publication Data

US 2009/0062842 A1     Mar. 5, 2009

(51) Int. Cl.
A61B 17/00     (2006.01)
(52) U.S. Cl. ..................................... 606/203
(58) Field of Classification Search ............. 606/201, 606/203
See application file for complete search history.

(56) References Cited

U.S. PATENT DOCUMENTS

| | | | |
|---|---|---|---|
| 35,038 A | 4/1862 | Pierce | |
| 1,500,629 A | 7/1924 | Levy | |
| 1,569,131 A | 1/1926 | Nord | |
| 1,606,841 A | 11/1926 | Newton | |
| 1,698,813 A | 1/1929 | Gouirand | |
| 2,084,412 A * | 6/1937 | Schaefer | 24/186 |
| 2,387,428 A | 10/1945 | Brothers | |
| 2,480,430 A | 8/1949 | Nugent | |
| 2,553,390 A | 5/1951 | Streyckmans | |
| 2,661,888 A | 12/1953 | Sidlinger | |
| 3,095,873 A | 7/1963 | Edmunds, Jr. | |
| 4,243,039 A | 1/1981 | Aginsky | |
| 4,273,130 A | 6/1981 | Simpson | |
| 4,526,165 A | 7/1985 | Mielnik, Jr. et al. | |

(Continued)

FOREIGN PATENT DOCUMENTS

| BE | 400213 | 1/1934 |
|---|---|---|
| GB | 2027149 | 2/1980 |

OTHER PUBLICATIONS

Calkins et al., May 2000, "Evaluation of Possible Battlefield Tourniquet Systems for the For-Forward Setting," Military Medicine, vol. 165(5):379-384.

(Continued)

Primary Examiner—Eduardo C Robert
Assistant Examiner—Kevin Everage
(74) Attorney, Agent, or Firm—Holme Roberts & Owen LLP

(57) ABSTRACT

A tourniquet for restricting a flow of blood in a body part comprises a first elongated member, and a second elongated member in slidable engagement with the first elongated member. In addition, the tourniquet includes a tensioning mechanism connected to the second elongated member, wherein a compressive force is applied to the body part upon applying a tensile force to the second elongated member using the tensioning mechanism. At least one embodiment of the present invention comprises a buckle having one or more of a raised intermediate bar and one or more teeth for contacting a portion of the first elongated member. The tourniquet is suited for emergency use, and may be applied by using only one hand. Thus, the tourniquet may be applied, manipulated and tightened by the wearer, even if the wearer is limited to the use of a single hand.

12 Claims, 8 Drawing Sheets

U.S. PATENT DOCUMENTS

| | | | |
|---|---|---|---|
| 4,794,656 | A | 1/1989 | Henley, Jr. |
| 5,690,672 | A | 11/1997 | Cohen |
| 5,993,362 | A | 11/1999 | Ghodai |
| 6,361,548 | B1 | 3/2002 | McEwen |
| 6,513,460 | B2 | 2/2003 | Fountoulakis |
| 6,537,298 | B2 | 3/2003 | Dedo |
| 6,540,707 | B1 | 4/2003 | Stark et al. |
| 6,544,188 | B1 | 4/2003 | Chesney et al. |
| 6,602,214 | B2 | 8/2003 | Heinz et al. |
| 6,605,103 | B2 | 8/2003 | Hovanes et al. |
| 6,682,547 | B2 | 1/2004 | McEwen et al. |
| 6,746,470 | B2 | 6/2004 | McEwen et al. |
| 6,796,993 | B2 | 9/2004 | Lambroza |
| 6,884,254 | B2 | 4/2005 | Brooks |
| 6,899,720 | B1 | 5/2005 | McMillan |
| 2001/0041910 | A1 | 11/2001 | McEwen |
| 2002/0016610 | A1 | 2/2002 | Hovanes et al. |
| 2002/0120288 | A1 | 8/2002 | Dedo |
| 2002/0188315 | A1 | 12/2002 | Guzman et al. |
| 2003/0028215 | A1 | 2/2003 | Brooks |
| 2003/0036771 | A1 | 2/2003 | McEwen et al. |
| 2003/0065357 | A1 | 4/2003 | Dedo et al. |
| 2003/0139766 | A1 | 7/2003 | McEwen et al. |
| 2003/0144691 | A1 | 7/2003 | Lambroza |
| 2003/0153936 | A1 | 8/2003 | El-Galley |
| 2003/0167070 | A1 | 9/2003 | McEwen et al. |
| 2003/0236548 | A1 | 12/2003 | Hovanes et al. |
| 2004/0147956 | A1 | 7/2004 | Hovanes et al. |
| 2005/0049630 | A1 | 3/2005 | Ambach |
| 2005/0113866 | A1 | 5/2005 | Heinz et al. |
| 2005/0143689 | A1 | 6/2005 | Ramsey, III |
| 2005/0240217 | A1 | 10/2005 | Jennifer et al. |
| 2005/0273134 | A1* | 12/2005 | Esposito ............... 606/203 |
| 2008/0221612 | A1* | 9/2008 | Rose ..................... 606/203 |

OTHER PUBLICATIONS

Crisp; Jul. 18, 2005, "New Tourniquet Issued to Deployed Soldiers"; Defend America News Article; 2 pp.

Holcomb, Jul. 28, 2004, "Tourniquet Recommendations from USAISR"; US Army Institute of Surgical Research; 2 pp.

Webpages for "The Ratchet Tourniquet," Chinook Medical Gear, Inc.; (at least as early as Jan. 20, 2005), 3 pp.

Statement for Information Disclosure Statement by Mark Esposito, signed Oct. 5, 2008 (3 page document).

Statement for Information Disclosure Statement by Mark Esposito, signed Oct. 5, 2008 (2 page document).

U.S. Appl. No. 12/163,796, filed Jun. 27, 2008, by Mark Esposito et al.

International Search Report and Written Opinion, mailed Oct. 3, 2008, for Application No. PCT/US2005/020111.

Office Action dated Sep. 16, 2009, issued in Israeli Application No. 179769.

Search Report dated Sep. 28, 2009, issued in European Application No. 05757785.0.

Office Action dated Dec. 10, 2009, issued in U.S. Appl. No. 11/147,806.

Brill et al. "Bier's Block; 100 Years Old and Still Going Strong!" ACTA Anaesthesiologica Scandinavica, 2004, No. 48, pp. 117-122.

Kam et al "The Arterial Tourniquet: Pathophysiological Consequences and Anaesthetic Implications", Anaesthesia, 2001, No. 56, Blackwell Science Ltd., pp. 534-545.

Klenerman, L. "The Tourniquet Manual—Principles and Practice," 2003, Springer-Verlag London Limited, Chap. 1, pp. 3-11.

McEwen et al. "Tourniquet Safety in Lower Leg Applications", Orthopaedic Nursing, vol. 21, No. 5, Sep./Oct. 2002.

Parsons, Donald L. et al., "Tourniquets—Lifesavers on the Battlefield", article published on www.professionalsoldiers.com dated Oct. 13, 2004.

U.S. Department of Labor et al. "First Aid Book", reprinted 1993, first publication date unknown, pp. 64-66.

Welling et al "A Balanced Approach to Tourniquet Use: Lessons Learned and Relearned", American College of Surgeons, vol. 203, No. 1, Jul. 2006, Elsevier, Inc.

Webpage from www.EBay.com for Non-Pneumatic Tourniquet Olive Drab, marketed by Specialized Equipment, printed Aug. 20, 2009.

Office Action dated Mar. 17, 2009, issued in U.S. Appl. No. 11/147,806.

Response to Office Action dated Aug. 14, 2009, filed in U.S. Appl. No. 11/147,806.

Final Office Action dated Jun. 8, 2010, issued in U.S. Appl. No. 11/147,806.

Notice of Allowance dated Sep. 28, 2010, issued in U.S. Appl. No. 11/147,806.

Office Action dated Jul. 7, 2010, issued in Israel Application No. 179769.

Office Action dated Mar. 22, 2010, issued in European Patent Application No. 05757785.0.

* cited by examiner

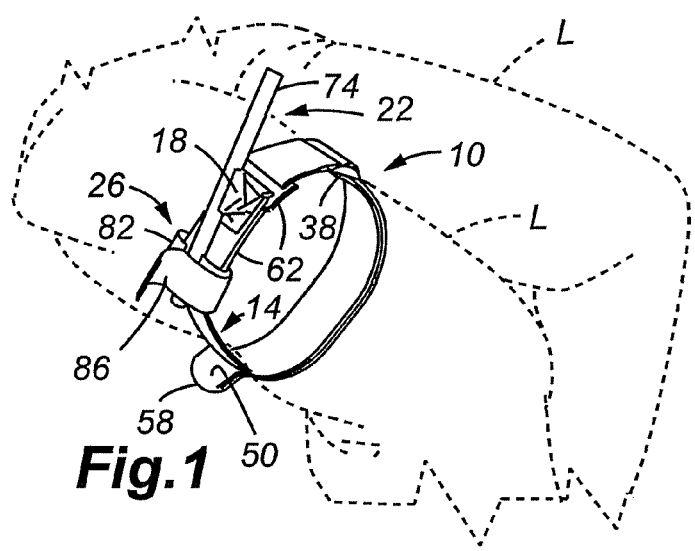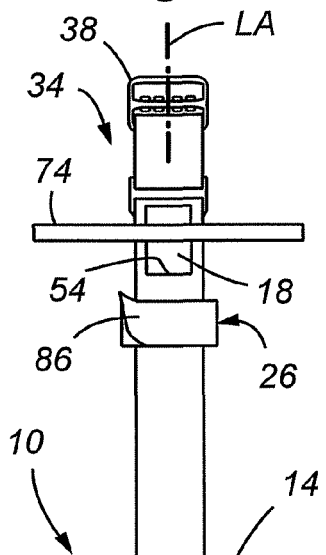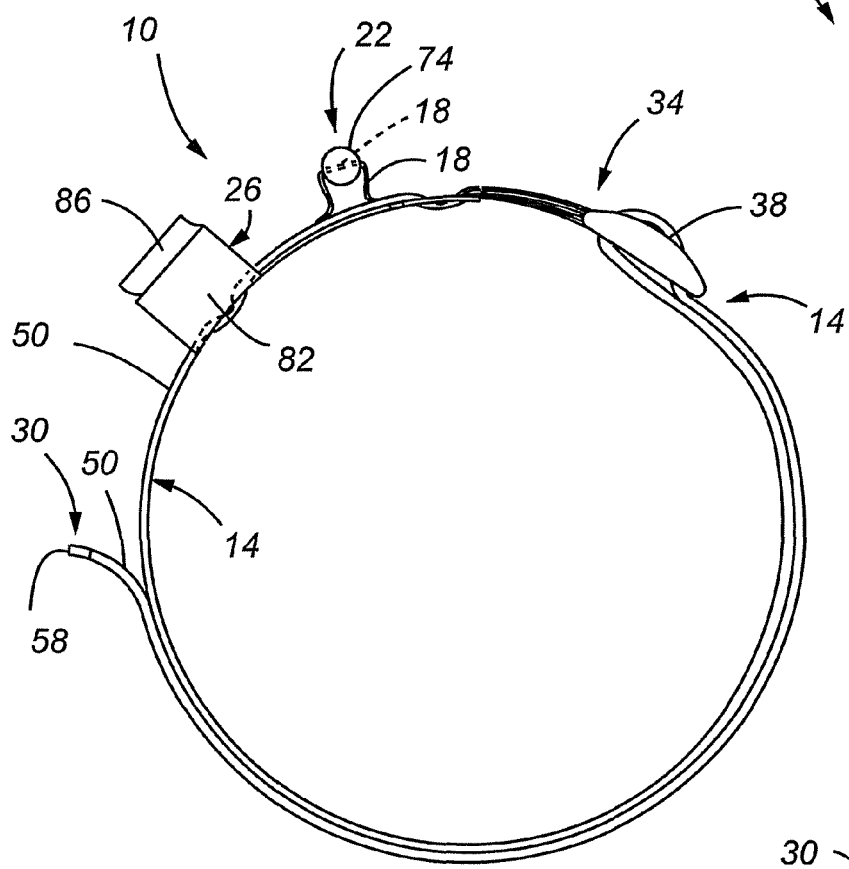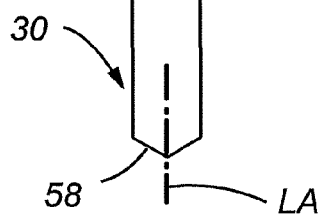

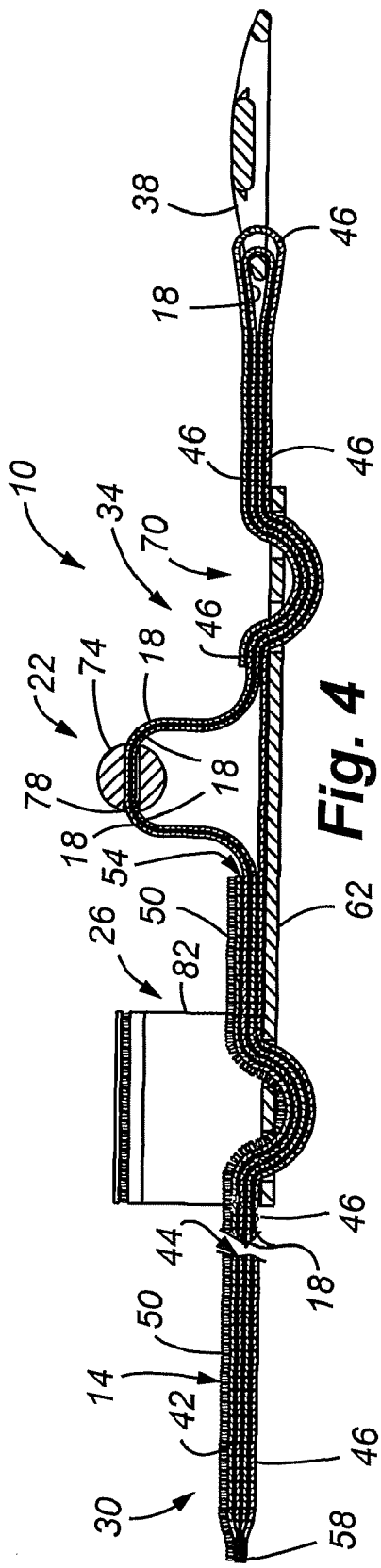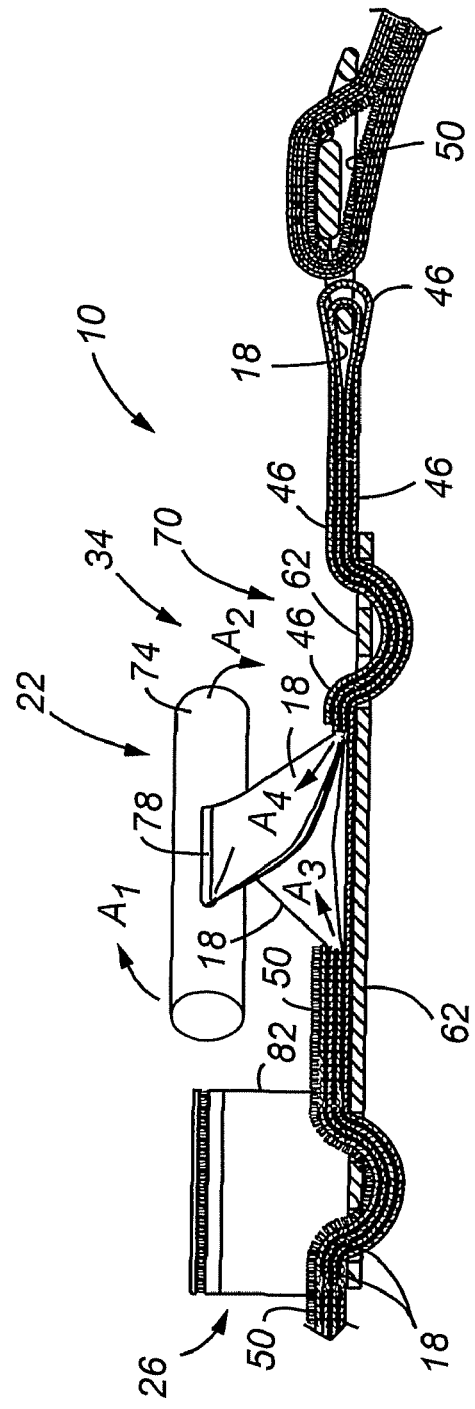

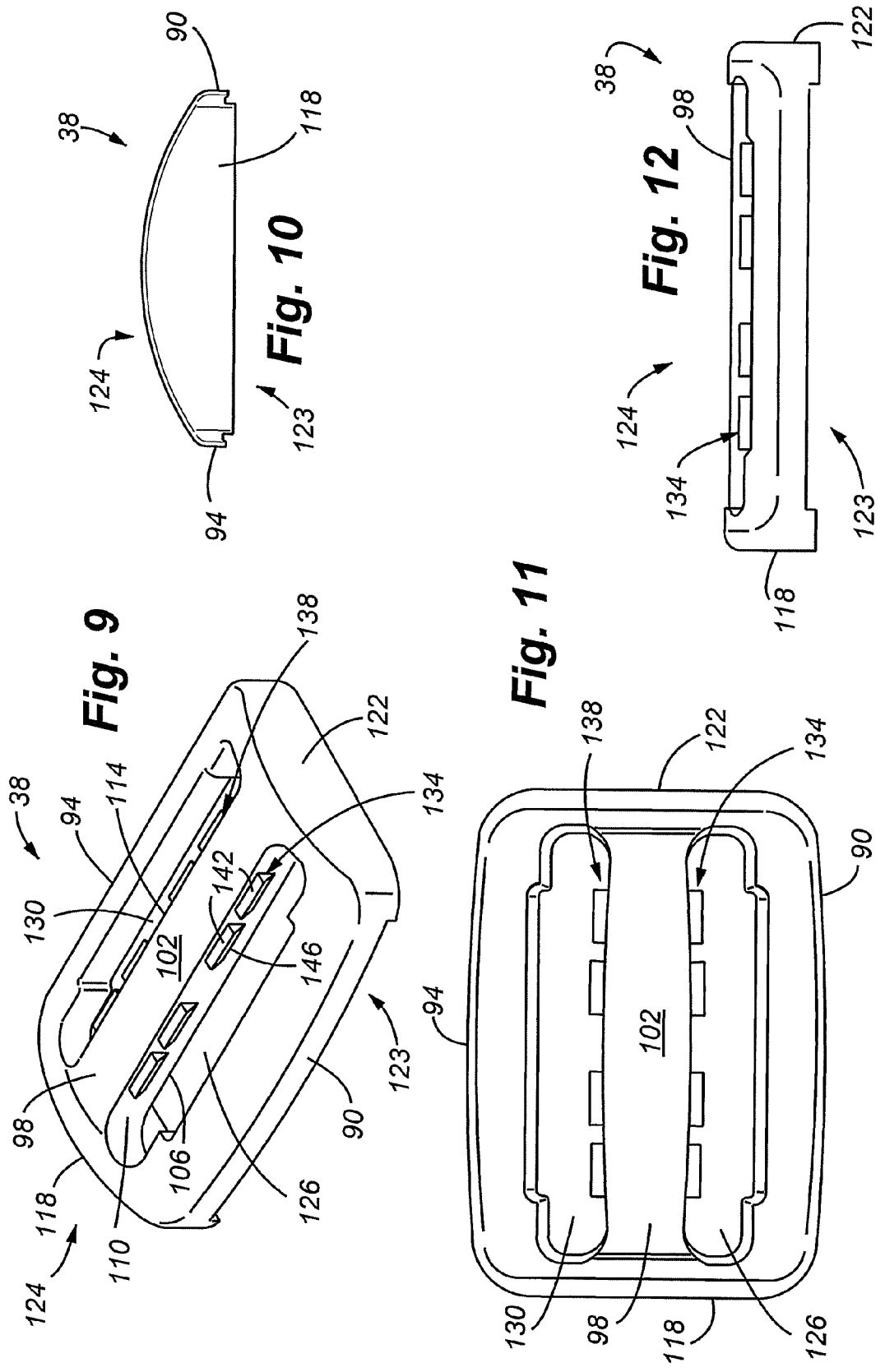

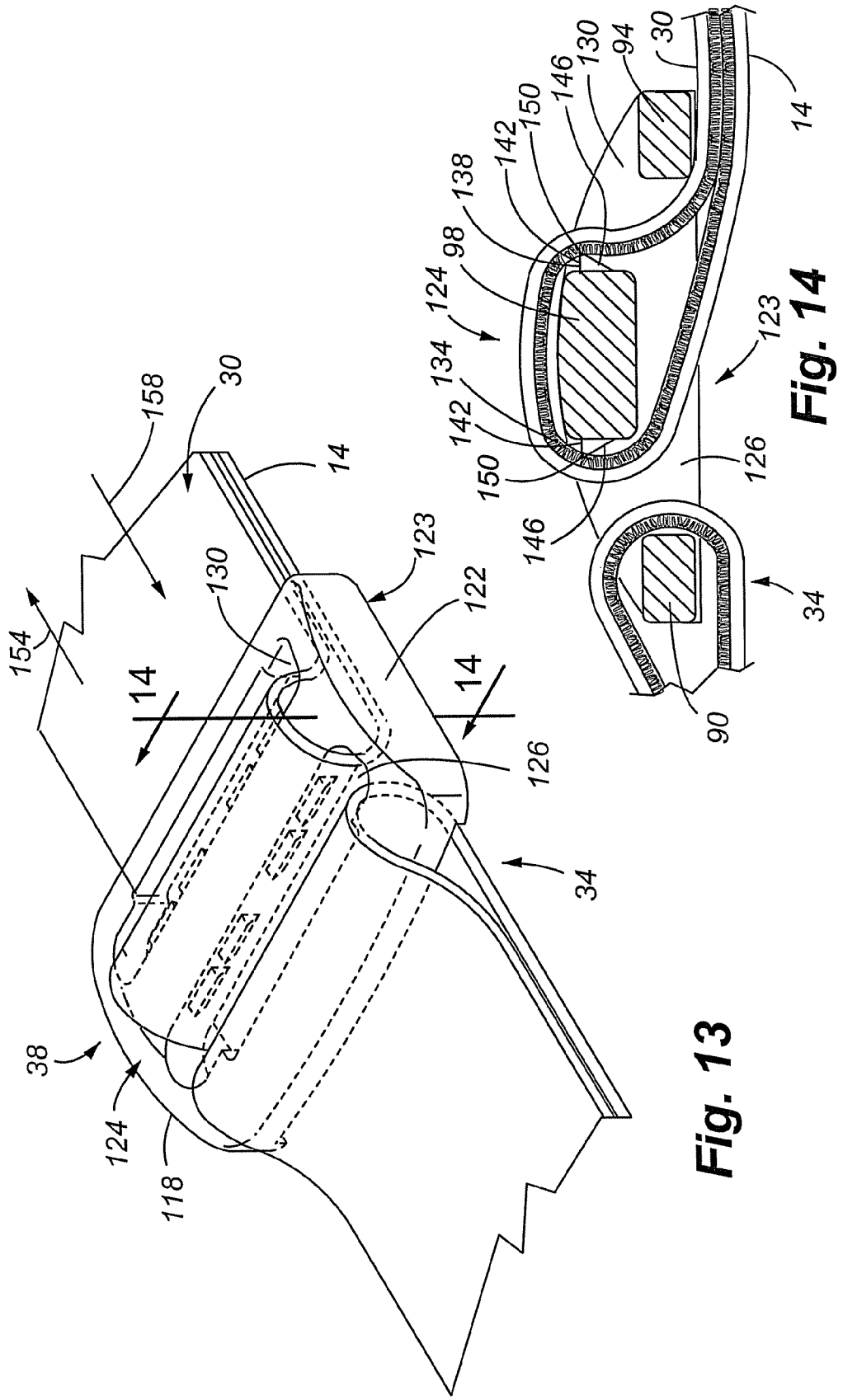

TOURNIQUET AND METHOD OF USE

CROSS REFERENCE TO APPLICATION

The present application cross references, but does not claim priority to U.S. patent application Ser. No. 11,147,806 entitled "Tourniquet and Method of Use" filed on Jun. 6, 2005, the entire disclosure of which is incorporated herein by reference in its entirety.

FIELD

The present invention relates to a novel flow restriction device, and more particularly, to a novel tourniquet device for restricting the flow of blood.

BACKGROUND

The following text should not be construed as an admission of knowledge in the prior art. Furthermore, citation or identification of any document in this application is not an admission that such document is available as prior art to the present invention, or that any reference forms a part of the common general knowledge in the art.

Loss of blood is a major cause of death in emergency situations in which the injured person is alone or medical assistance is not immediately available. The use of a tourniquet to stop blood loss from an injured arm or leg is a well-known technique for preventing death in these situations. In general, for emergency use where the victim is alone, the victim must be able to apply the tourniquet to his or her own arm or leg and occlude blood flow using only one hand.

Tourniquets of the prior art generate inward radial compression on the limb by being put into high levels of circumferential tension when wrapped around the limb. As the pressure on the limb increases, the friction between the strap and the limb also increases, causing the underlying soft tissue to move with the strap as it is drawn tight. This tends to draw soft tissues underlying the strap into the ratchet or buckle device, pinching the soft tissue and creating a region of very high localized pressure which will cause unnecessary injury. This effect may also create high shearing stresses in the underlying soft tissues, increasing the probability of nerve and tissue injury. Friction between the strap and the limb may also create regions of low pressure by preventing tension from being distributed evenly in the strap around the entire limb circumference, and as a result, arterial blood may still flow through these low pressure regions although overall strap tension is very high. In general, the application of uneven or non-uniform application of pressure around the limb leads to the need for unnecessarily high overall tourniquet pressures to reliably and predictably stop arterial blood flow, and this need for unnecessarily high pressure increases the probability of a range of unnecessary injuries to nerves, muscles and the limb.

The use of a tourniquet in many emergency situations, including many recreational activities, such as hiking, rock climbing and camping, imposes a weight restriction on the tourniquet. Simply stated, if a tourniquet is too bulky or has an excessive weight, the potential user, such as a hiker, will not pack and carry the tourniquet with them. Therefore, there is a need of a relatively small and light-weight tourniquet that can be easily packed and carried, and subsequently used at remote locations, if necessary.

Accordingly, there is a need for an emergency, light-weight tourniquet that provides improved radial pressure to the wounded limb, thereby restricting blood flow to the limb. Furthermore, there is a need for such a tourniquet that can be applied by the victim using one hand.

SUMMARY

These and other needs are addressed by the various embodiments and configurations of the present invention. The present invention comprises a tourniquet for restricting the flow of blood in a body part, such as a person's arm or leg.

It is to be understood that the present invention includes a variety of different versions or embodiments, and this Summary is not meant to be limiting or all-inclusive. This Summary provides some general descriptions of some of the embodiments, but may also include some more specific descriptions of certain embodiments.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

In accordance with embodiments of the present invention, a tourniquet for restricting a flow of blood in a body part comprises an outer sleeve having first and second ends, a buckle connected to the second end of the outer sleeve, an inner strap in slidable engagement with the outer sleeve, and a windlass connected to the inner strap. The windlass applies tensile force to the inner strap, which applies a compressive force to the body part thus restricting the flow of blood in the body part. The buckle generally includes a top and a bottom, first and second lateral sides that are spaced apart from each other, and an intermediate bar located between the first and second lateral sides, the intermediate bar including top and bottom surfaces with first and second sidewalls therebetween. The intermediate bar of the buckle further includes at least one first tooth situated on one of the first and second sidewalls of the intermediate bar to assist in preventing the outer sleeve from disengaging from the buckle.

In accordance with embodiments of the present invention, a first port may be located between the intermediate bar and the first lateral side of the buckle such that the at least one first tooth extends into the first port from the first sidewall of the intermediate bar. Further, the at least one or more additional teeth may extend into the first port from the first sidewall of the intermediate bar. The at least one first tooth may comprise a top surface that is generally parallel to the top surface of the intermediate bar, an inclined surface, and a projection situated between the top surface of the at least one first tooth and the inclined surface. In some variations, the inclined surface generally faces toward the bottom of the buckle. In other variations, the inclined surface generally faces toward the top of the buckle. Additionally, in accordance with other embodiments of the present invention, in addition to the at least one first tooth, the intermediate bar may include a top surface that is elevated with respect to first and second ends of the buckle.

The present invention includes a variety of possible configurations. Thus, in accordance with embodiments of the present invention, a tourniquet for restricting a flow of blood in a body part is provided, the tourniquet comprising an outer sleeve having first and second ends, a buckle connected to the second end of the outer sleeve, an inner strap in slidable engagement with the outer sleeve, and a windlass connected to the inner strap. The windlass applies tensile force to the inner strap, which applies a compressive force to the body part thus restricting the flow of blood in the body part. The buckle generally includes a top and a bottom, first and second lateral sides that are spaced apart from each other, and an intermediate bar located between the first and second lateral sides, the intermediate bar including top and bottom surfaces with first and second sidewalls therebetween. The intermediate bar of the buckle further includes a top surface that is elevated with respect to first and second ends of the buckle to assist in preventing the outer sleeve from disengaging from the buckle. In accordance with embodiments of the present invention, a first port may be located between the intermediate bar and the first lateral side of the buckle such that the at least one first tooth extends into the first port from the first sidewall of the intermediate bar.

The present invention also includes a method of restricting a flow of blood to a body part. The method comprises wrapping a first elongated member with a buckle on a second portion thereof around the body part, the buckle having first and second ports with at least one tooth extending into each of the first and second ports. Moreover, the method includes threading a first portion of the first elongated member through the first port in the buckle from the bottom to the top of the buckle, and extending the first portion of the first elongated member over an intermediate bar of the buckle. Further, the method includes threading the first portion of the first elongated member through the second port in the buckle from the top to the bottom of the buckle such that each of the teeth in the first and second ports are in contact with the first elongated member, and detachably attaching the first portion of the elongated member to an outer surface of the elongated member so as to mount the first elongated member to the body part. Additionally, the method can include operating a tensioning mechanism operatively connected to a second elongated member slidably positioned relative to the first elongated member, wherein the tensioning mechanism develops a tensile force in the second elongated member, wherein a compressive force is applied to the body part restricting the flow of blood in the body part.

In accordance with embodiments of the present invention, a tourniquet for restricting a flow of blood in a body part is provided, the tourniquet comprising means for circumferentially surrounding the body part, means for detachably connecting first and second ends of the means for surrounding, means for compressing the body part, and means for tensioning the means for compressing. The means for compressing slidably engages the means for circumferentially surrounding, and applying a tensile force to the means for compressing using the means for tensioning applies a compressive force to the body part to restrict the flow of blood in the body part. In one embodiment the means for detachably connecting comprises first and second means for receiving the means for surrounding, and first and second means for providing drag to the means for surrounding, located within the first and second means for receiving, respectively. Further, the first end of the means for surrounding can be looped around the body part and through the first and second means for receiving so as to mount the means for surrounding around the body part. Additionally, the means for surrounding can interact with the means for providing drag to prevent the means for surrounding from disengaging from the means for detachably connecting.

In accordance with embodiments of the present invention, a tourniquet for restricting a flow of blood in a body part is provided, the tourniquet comprising means for circumferentially surrounding the body part, means for detachably connecting first and second ends of the means for surrounding, means for compressing the body part, and means for tensioning the means for compressing. The means for compressing slidably engages the means for circumferentially surrounding, and applying a tensile force to the means for compressing using the means for tensioning applies a compressive force to the body part to restrict the flow of blood in the body part. In one embodiment the means for detachably connecting comprises first and second means for receiving the means for surrounding, and means for converting an input load into an output load that provides a pressure on the means for surrounding. Further, the first end of the means for surrounding can be looped around the body part and through the first and second means for receiving so as to mount the means for surrounding around the body part. Moreover, the means for surrounding can provide the input load to the means for converting which prevents the means for surrounding from disengaging from the means for detachably connecting once the means for surrounding is mounted around the body part.

Various embodiments of the present invention are set forth in the attached figures and in the detailed description of the invention as provided herein and as embodied by the claims. It should be understood, however, that this Summary may not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

FIG. 1 is a perspective view of an embodiment of the present invention applied to a person's right leg (as shown in dashed lines);

FIG. 2 is a plan view of the device shown in FIG. 1, where the device is stretched out along its longitudinal axis;

FIG. 3 is a side elevation view of the device shown in FIG. 1, where the device is shown prior to tightening the device using the windlass;

FIG. 4 is a cross sectional view of the device shown in FIG. 2 with the windlass in an unwound position;

FIG. 5 is the same cross section view of the device as shown in FIG. 4, but with the outer sleeve looped through the buckle and the windlass partially rotated;

FIG. 9 is a perspective view of a buckle of the device according to one embodiment of the present invention;

FIG. 10 is a side elevation view of the buckle of FIG. 9 according to one embodiment of the present invention;

FIG. 11 is a plan view of the buckle of FIG. 9 according to one embodiment of the present invention;

FIG. 12 is a front view of the buckle of FIG. 9 according to one embodiment of the present invention;

FIG. 13 is a perspective view of the buckle of FIG. 9 showing the first end of the outer sleeve being looped through the first and second ports of the buckle according to one embodiment of the present invention;

FIG. 14 is a cross sectional view of a portion of the buckle of FIG. 9 illustrating the interaction of the first and second tooth sets with the outer sleeve;

Figure 6:
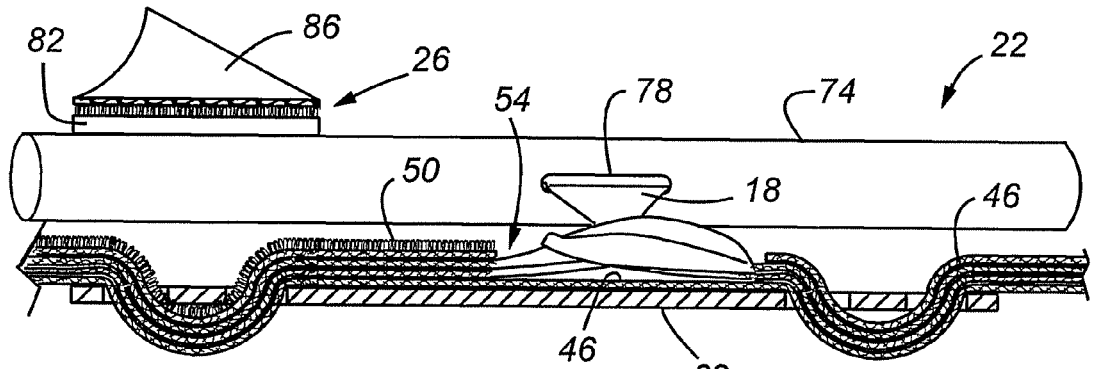
FIG. 6 is a cross sectional view of a portion of the device with the windlass in a wound position.

The drawings are not necessarily to scale, and may, in part, include exaggerated dimensions for clarity.

DETAILED DESCRIPTION

The present invention comprises a tourniquet that can be manipulated and tightened by the user, including the victim, using one hand, if necessary. In addition, the tourniquet provides improved circulation stoppage by way of an inner tightening strap positioned within a sleeve.

Referring now to FIG. 1, a tourniquet 10 in accordance with embodiments of the present invention is shown. The tourniquet 10 comprises a first elongated member or an outer sleeve 14, a second elongated member, inner tightening member or inner strap 18, a tightening mechanism 22 and a securing mechanism 26. As shown in FIG. 1, the tourniquet 10 can be applied to an appendage, as for example, leg L, and then tightened to restrict the flow of blood to the leg L.

Referring now to FIG. 2, the tourniquet 10 is shown prior to use, or in a stretched-out orientation. The outer sleeve 14 comprises a longitudinally extensive material having a first end 30 and a second end 34. In accordance with embodiments of the present invention, the second end 34 includes a restraining mechanism comprising a buckle 38. When the tourniquet 10 is applied to a limb, such as leg L shown in FIG. 1, the first end 30 is looped through the buckle 38 and pulled tight around the appendage, thus providing a means for circumferentially surrounding or encircling the limb. FIG. 3 depicts the tourniquet 10 after the first end 30 has been looped through the buckle 38.

Referring now to FIG. 4, in accordance with embodiments of the present invention, the outer sleeve 14 may be formed of two panels comprising an upper or first panel 42 and a lower or second panel 46. The edges of the panels 42 and 46 are connected, as for example, by sewing, gluing, stapling, clamping, or heat/ultra-sound (sonic) welding, or combinations thereof. Outer sleeve 14 includes a pocket, interior area or inner space 44 between the panels 42 and 46. The first panel 42 comprises an outer surface 50 that preferably includes hook and loop structures. More preferably, the outer surface 50 comprises both hook structures and loop structures along substantially the entire length of the outer sleeve 14 between the first end 30 and an opening 54 where the inner strap 18 is exposed between the first panel 42 and second panel 46 of the outer sleeve 14. Thus, when the first end 30 of the outer sleeve 14 is looped through the buckle 38, the outer surface 50 may be applied to itself, thereby securing the position of the outer sleeve 14. By way of example and not limitation, the first panel 42 may comprise a length of OMNI-TAPE® (Velcro Industries B.V., Amsterdam, Netherlands), wherein the fastening surface comprises both hook and loop structures on the outer surface 50 as depicted in FIG. 4. The use of a combination of both hook and loop structures on the outer surface 50 of the outer sleeve 14 provides the advantage of the tourniquet being quickly adjustable when in use to accommodate a variety of size appendages, as for example, from a person's thigh to a person's forearm.

In use, to size the tourniquet to the appendage, the user simply wraps the tourniquet around the subject appendage, loops the first end 30 of the outer sleeve 14 through the buckle 38, pulls the tourniquet reasonably tight, and then presses the outer surface 50 together detachably interlocking first and second portions of the outer surface 50 together to interlock the hook and loop structures of the outer surface 50 within the region where the outer surface 50 overlaps beyond the buckle 38. As those skilled in the art will appreciate, although not preferred, the outer surface 50 of the outer sleeve 14 may be fitted with standard hook fasteners to match-up with corresponding standard loop fasteners; however, although within the scope of the present invention, the ability of a single tourniquet so modified to accommodate various size appendages would be limited. Nonetheless, such an issue could be addressed by manufacturing tourniquets of different sizes and/or providing tourniquets having different portions of the outer surface fitted with various lengths of hook material to match-up with corresponding portions of loop material. Alternatively, other means of fastening the overlapping portion of the outer sleeve may be provided, such as buttons, snaps, transverse straps etc., and such variations and modifications are within the scope of the present invention.

It is further noted that although the outer sleeve 14 is preferably formed of an upper or first panel 42 and a lower or second panel 46, the outer sleeve 14 may be formed of a single piece of material, as by way of example and not limitation, a piece of material that is folded over and seamed, thereby forming a pocket or inner space 44.

Referring still to FIG. 4, the inner strap 18 is shown between the first panel 42 and the second panel 46 of the outer sleeve 14. In accordance with at least one embodiment of the present invention, the inner strap 18 comprises a length of nylon binding strap (also known as nylon binding tape) that extends from first end 30 of the outer sleeve 14 to the buckle 38 and returns to the first end 30 such that the inner strap 18 comprises a loop. Although a substantially non-elastic nylon binding strap type of material is preferred for use as the inner strap 18, other elongated types of materials may be used, such as a section of rope, belt, tubing, hose, band, or combinations thereof, where such structures thereby form a means for compressing a body part. The ends of the inner strap 18 are preferably anchored only at the tip 58 of the first end 30 of outer sleeve 14, as for example, by sewing, gluing, stapling, clamping, or heat/ultra-sound (sonic) welding, or combinations thereof. Thus, the inner strap 18 can slide within the interior space 44 of the outer sleeve 14. Accordingly, the inner strap 18 comprises a material that has frictional characteristics allowing it to slide within the interior space 44 of the outer sleeve 14 when a tensile force is applied to the inner strap 18. Although not required, depending upon the types of materials used to form the outer sleeve 14 and the inner strap 18, the interior space 44 of the outer sleeve 14 may optionally include a substance, such as a powder or other lubricant, to assist with the frictional characteristics between the surfaces of the inner strap 18 and the interior space 44 of the outer sleeve 14.

In accordance with embodiments of the present invention, the tourniquet may comprise an inner strap 18 that extends through and end or a slit (not shown) at the first end 30, such as a slit in the upper or first panel 42 of the outer sleeve 14. The inner strap 18 may then be anchored at or proximate to the distal end of the lower or second panel 46. Alternatively, the slit (not shown) may be in the second panel 46 and the inner strap 18 anchored at or proximate to the distal end of the first panel 42.

In accordance with embodiments of the present invention, the tourniquet may be configured such that a single layer (i.e., not a loop) of material is used to form the inner strap 18. Here, a first end of the inner strap 18 is anchored at or near the tip 58 of the first end 30 of the outer sleeve 14, and a second end of the inner strap 18 is anchored at or near the buckle 38, with the middle portion not anchored to the outer sleeve 14, and thereby able to slide within the outer sleeve 14. The tensioning mechanism 22 can be used to tighten the inner strap 18, such as by winding the windlass 74 to develop a tension force in the inner strap 18.

Referring still to FIG. 4, in accordance with embodiments of the present invention, the tourniquet 10 preferably includes a base member 62. As by way of example and not limitation, the base member 62 may be formed of a KYDEX® (Kleerdex Company, LLC, Mount Laurel, N.J.) thermoplastic or moldable (as for example, injection molded) plastic type of material. A first end 66 of base member 62 preferably includes a securing mechanism 26, as will be discussed below. The second panel 46 of the outer sleeve 14 extends over at least a portion of the base member 62, passes through a means for looping, such as buckle 38, and folds back to a second end 70 of the base member 62. The edges of the second panel 46 between the buckle 38 and the second end 70 of the base member 62 are preferably connected, as for example, by sewing, gluing, stapling, clamping, or heat/ultra-sound (sonic) welding, thereby securing the second end 34 of the outer sleeve 14 to the buckle 38.

Referring still to FIG. 4, in accordance with embodiments of the present invention, the inner strap 18 emerges from the outer sleeve 14 at opening 54 where it is connected to the tightening mechanism 22. For the embodiment shown in FIG. 4, the tightening mechanism 22 comprises a windlass 74 that is shown in an unwound position. The windlass 74 preferably is comprised of a plastic material; however other types of materials are within the scope of the invention. In accordance with embodiments of the present invention, the inner strap 18 passes through a slot or aperture 78 in the windlass 74, and as described above, the inner strap 18 extends to and around the buckle 38.

Figure 7:
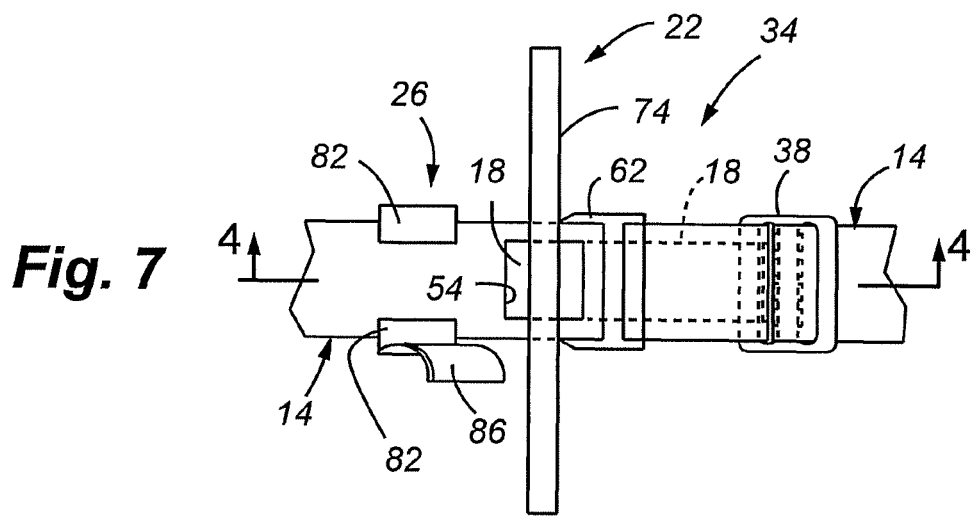
FIG. 7 is a plan view of the buckle end of the device with the outer sleeve looped through the buckle and the windlass in an unwound position.

Referring to FIG. 7, a plan view of the second end 34 of the outer sleeve 14 is shown. Here, the outer sleeve 14 has been looped through buckle 38; however, the tension mechanism 22, comprising a windlass 74, as will be described below, has not been wound to tighten the inner strap 18.

Figure 8:
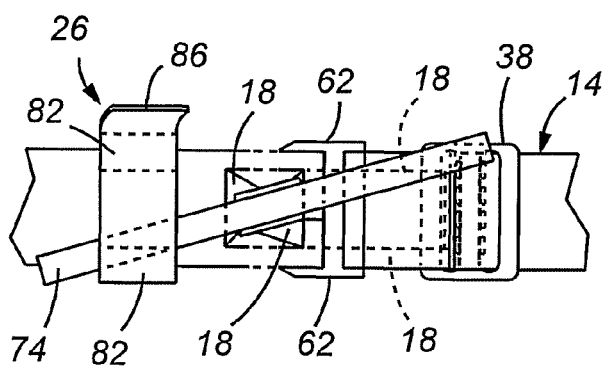
FIG. 8 is a plan view of the buckle end of the device with the outer sleeve looped through the buckle and the windlass in a wound position.

Referring now to FIG. 8, a plan view of the second end 34 of the outer sleeve is shown. Here, the outer sleeve 14 has been looped through buckle 38 and the windlass 74 has been partially wound, thereby applying a tensile force to the inner strap 18. Since the end of the inner strap 18 is secured to the tip 58 of the outer sleeve 14, when the windlass 74 is rotated, the inner strap 18 slides within the outer sleeve 14, essentially scrunching the outer sleeve 14 relative to the inner strap 18 as the inner strap 18 is increasingly tightened. The tightened inner strap 18 provides a substantially even radial compressive pressure to the limb to which the tourniquet 10 is being applied.

Referring now to FIG. 5, a cross sectional view of the tourniquet 10 is shown, including the second end 34 of tourniquet 10 with the windlass 74 in a partially wound position. More particularly, in use, after the first end 30 of the outer sleeve 14 is passed through the buckle 38 and secured around an appendage or limb, such as leg L shown in FIG. 1, the windlass 74 is rotated, such as in the direction of arrows A1 and A2, to apply a tensile force to at least a portion of the inner strap 18. Since the inner strap 18 is secured to the tip 58 of first end 30 of the outer sleeve 14, the inner strap 18 slides in the direction of arrows A3 and A4 within the outer sleeve 14 as the windlass 74 is rotated, thereby pulling the inner strap and providing a circumferentially applied compression force to the appendage. The tensile force is primarily developed in the portion of the inner strap 18 between the buckle 38 and the windlass 74, with typically a lesser amount of tension developed in the overlapping portion of the inner strap 18 between the buckle 38 and the tip 58, because when the inner strap 18 bends around the buckle 58 after being applied to an arm or leg, the bend tends to prevent the slippage of the inner strap 18 in the overlapped portion. After the windlass 74 is tightened, the tourniquet restricts the blood flow in the appendage. Accordingly, the tourniquet 10 of the present invention offers the advantage of an unlimited number of possible twists. More particularly, many tourniquets of the prior art are limited to a set number to twists by their windlass, thus limiting the amount of possible compression. As a result, such tourniquets of the prior art are venous tourniquets and are not suitable for arterial occlusion. However, the combination of the outer sleeve 14, inner strap 18 and tightening mechanism 22 of the present invention overcome this prior art limitation.

Referring now to FIG. 6, a cross sectional view of the second end 34 of tourniquet 10 is shown with the windlass 74 in a wound position. In accordance with embodiments of the present invention, after the windlass 74 has been sufficiently tightened to restrict the arterial blood flow in the appendage, the windlass 74 may be secured using securing mechanism 26. The securing mechanism 26 provides a means for securing or preventing the windlass 74 from unwinding. Thus, the securing mechanism 26 maintains the wound position of the windlass 74, and thereby maintains the tension in the inner strap 18.

In accordance with embodiments of the present invention, and as best seen in FIGS. 1, 7, and 8, the securing mechanism 26 preferably comprises a pair of opposing hooked catches 82 set substantially transverse to the longitudinal axis L-L of the tourniquet 10. More particularly, the hooked catches 82 are preferably sized to cup or hold the windlass, or a portion thereof, and prevent it from unwinding. Accordingly, the hooked catches 82 are sufficiently stiff to provide adequate resistance against the tensile force within the inner strap 18, as transferred to the hooked catches by the windlass 74. In accordance with embodiments of the present invention, and by way of example and not limitation, the hooked catches 82 may be formed of a KYDEX® thermoplastic material or molded plastic that may be integrally formed with, or otherwise connected to the base member 62. The preferred use of two opposing catches 82 allows the user to rotate the windlass 74 in either direction, with one of the two catches 82 always able to prevent the windlass 74 from unwinding. However, it is to be understood that the use of a single hooked catch 82 may be used and is within the scope of the present invention. For a single hooked catch 82, the user must rotate the windlass in the proper direction to allow the tension in the inner strap 18 to be resisted by the single hooked catch 82 once winding of the windlass and tensioning of the inner strap 18 is completed.

In accordance with embodiments of the present invention, the securing mechanism 26 may comprise a securing strap positioned transversely to a longitudinal axis L-L of the outer sleeve 14. As for example, a transversely oriented strap having hook and loop fastening portions, or an elastic band engaging a hook or button may be provided to secure the windlass 74 in its wound position.

In yet another possible alternative, a transversely oriented strap 86 may be used in combination with the hooked catches 82. Such a combination of structures allows the user to secure the windlass 74 and move about (or be moved by another person) with less concern of the windlass 74 dislodging from the hooked catches 82 and unwinding. In accordance with embodiments of the present invention, for hooked catches 82 used in combination with a transversely oriented strap 86, the outer surface of the hooked catches may comprise a hook or loop material, and a surface of the strap 86 may comprise a complementary hook or loop material to interlock with the material on the hooked catches 82.

With reference to FIGS. 9-12, an embodiment of a buckle 38 is shown for use in the above-described embodiments of the present invention. As previously described, the first end 30 of the outer sleeve 14 is looped through the buckle 38 and pulled tight around the appendage to allow the outer sleeve 14 to circumferentially surround or encircle the appendage. More specifically, the buckle 38 includes a first lateral side 90, a second lateral side 94, and an intermediate bar 98 generally parallel to and located between the first lateral side 90 and the second lateral side 94. The intermediate bar 98 includes a top surface 102, a bottom surface 106, and a first sidewall 110 and a second sidewall 114 located between the top surface 102 and bottom surface 106. A first end 118 and a second end 122 of the buckle 38 interconnect the first lateral side 90, second lateral side 94, and intermediate bar 98. Located between the first lateral side 90 and the intermediate bar 98 is a first port 126, and formed between the second lateral side 94 and the intermediate bar 98 is a second port 130. Each port provides a route or pathway for the looping outer sleeve 14 through the buckle 38 during tightening and loosening of the outer sleeve around the appendage.

Referring now to FIGS. 9, 13 and 14, the first port 126 includes a first tooth set 134 mounted to the first sidewall 110, and the second port 130 includes a second tooth set 138 mounted to the second sidewall 114 of the intermediate bar 98 for inhibiting movement of the outer sleeve 14 with respect to the buckle 38. Each tooth set 134 and 138 comprises at least one tooth. With reference to FIG. 14, each tooth includes a top surface 142, an inclined surface 146, and an edge or projection 150 therebetween. During operation and with respect to FIG. 13, the first end 30 of the outer sleeve 14 is fed through the first port 126 from the bottom 123 to the top 124 of the buckle 38, over the intermediate bar 98, and then through the second port 130 from the top 124 to the bottom 123 of the buckle 38. After the first end 30 has exited the second port 130 and been pulled to a desired tightness around the appendage, the hook and loop fastener on the bottom surface 50 of the first end 30 of the outer sleeve 14 is mated with the hook and loop fastener on the bottom surface 50 of the remainder of the outer sleeve 14 in order to secure the outer sleeve 14 around the appendage.

Referring still to FIGS. 13 and 14, a more detailed view illustrating the interaction between the first tooth set 134 and second tooth set 138 and the outer sleeve 14 is shown. More specifically, once the first end 30 of the outer sleeve 14 has been fed through the first port 126 and second 130 ports, the projections 150 of the first tool set 134 and second tooth set 138 of the first port 126 and second port 130 engage with the hooks and loops on the outer surface 50 of the outer sleeve 14. This increases the drag on the outer sleeve 14, thus providing resistance to the free movement of the outer sleeve 14 relative to the buckle 38. This drag is especially useful in situations when the hook and loop fastener on the bottom surface of the first end 30 of the outer sleeve 14 accidentally detaches from the hook and loop fastener on the outer surface 50 of the remainder of the outer sleeve 14. Thus, the one or more teeth provide an extra safety mechanism to prevent inadvertent disengagement of the first end 30 of the sleeve 14 from the buckle 38 when, for instance, a patient utilizing the tourniquet 10 is moved, dragged, crawls, etc. Further, those of ordinary skill in the art will appreciate how the inclined surface 146 of the first tooth set 134 facilitates movement of the outer sleeve 14 in a tightening direction of travel 154 while the inclined surface 146 of the second tooth set 138 facilitates movement of the outer sleeve 14 in a loosening direction of travel 158.

Figure 15:
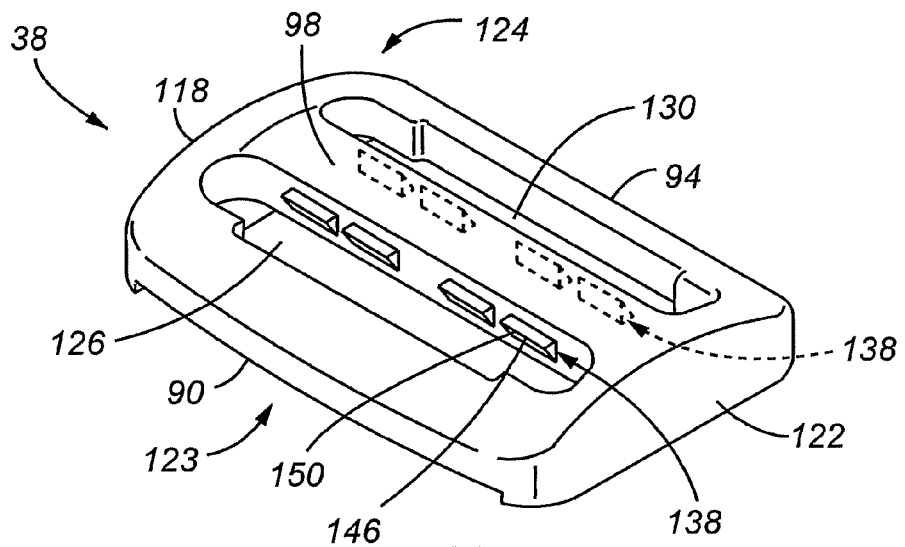
FIG. 15 is a perspective view of a buckle of the device according to another embodiment of the present invention with a second tooth set inverted relative to a first tooth set.
Figure 16:
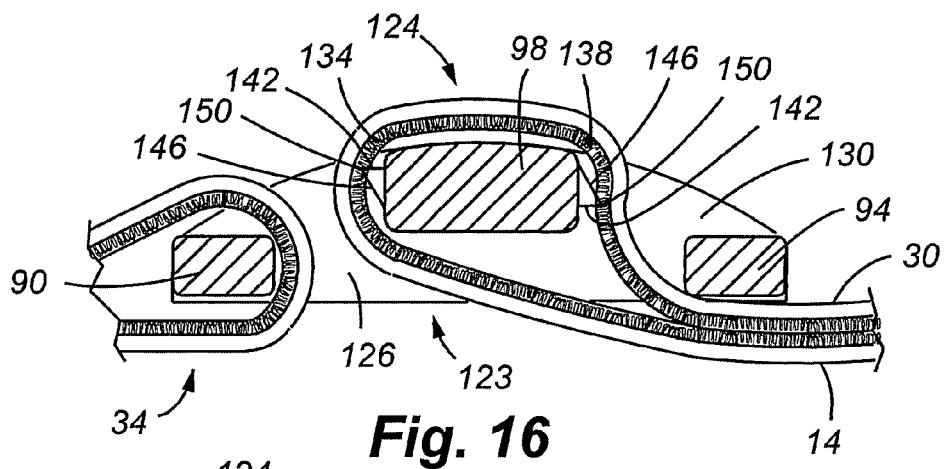
FIG. 16 is a cross sectional view of a portion of the buckle of FIG. 15 illustrating the interaction of the first and second tooth sets with the outer sleeve.

With respect to FIGS. 15 and 16, a variation of the buckle 38 is illustrated. More specifically, the second tooth set 138 is inverted relative to the first tooth set 134. Thus, movement of the outer sleeve 14 in a tightening direction of travel 154 is greatly facilitated due to the interaction of the inclined surfaces 146 of the first tooth set 134 and second tooth set 138 with the outer surface 50 of the outer sleeve 14. However, the drag on the outer surface 50 of the outer sleeve 14 in a loosening direction of travel 158 of the outer sleeve 14, such as from inadvertent loosening of the hooks and loops, is greatly increased due to the interaction of the projections 150 of the first tooth set 134 and second tooth set 138 with the outer surface 50 of the outer sleeve 14. Such an arrangement will greatly prevent inadvertent disengagement of the first end 30 of the outer sleeve 14 from the buckle 38. It will be appreciated that either of the first tooth set 134 and second tooth set 138 can be inverted while the other is not, or both of the first tooth set 134 and second 138 tooth set can be inverted or not inverted, in order to satisfy specific functional preferences.

Figure 17:
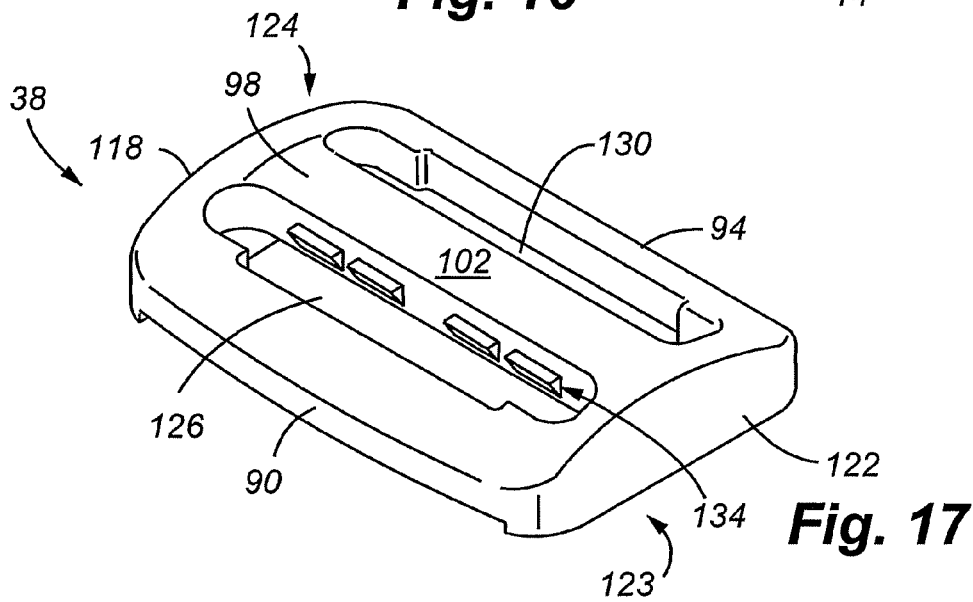
FIG. 17 is a perspective view of a buckle of the device according to another embodiment of the present invention with only a single tooth set.

Referring now to FIG. 17, and in accordance with another embodiment of the buckle 38, only a first tooth set 134 is provided on the buckle. Such an arrangement would be advantageous to simplify manufacturing of the buckle in addition to facilitating tightening and loosening movement of the outer sleeve 14 within the buckle 38. While the first tooth set 134 is illustrated as being situated in the first port 126, ordinary artisans will appreciate that the first tooth set 134 could be situated in the second port 130 if desired. Additionally, it is contemplated that the tooth set could be inverted so as to provide a desired amount of drag during loosening or tightening movement of the outer sleeve 14.

Figure 18:
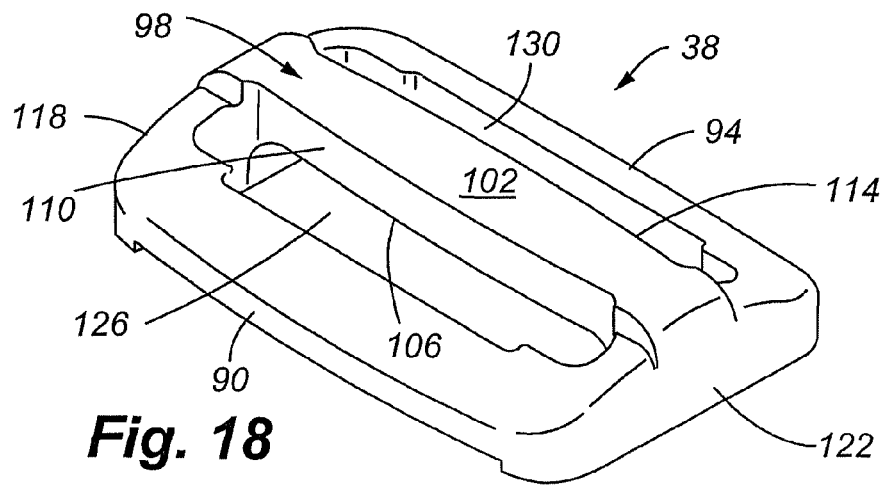
FIG. 18 is a perspective view of a buckle of the device according to another embodiment of the present invention with an elevated intermediate bar.
Figure 19:
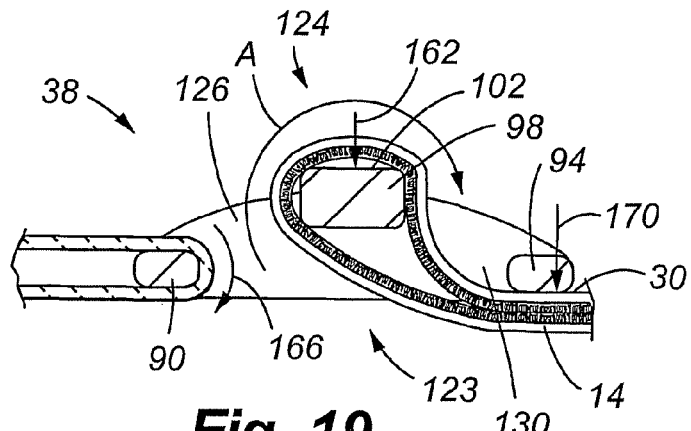
FIG. 19 is a side elevation view of the buckle of FIG. 18 showing the first end of the outer sleeve being looped through the first and second ports of the buckle according to another embodiment of the present invention.

With reference now to FIGS. 18 and 19, another embodiment of the buckle 38 is shown. Similar to previous embodiments, the buckle 38 includes first lateral side 90 and second lateral side 94, first end 118 and second end 122, first port 126 and second port 130, and an intermediate bar 98. The intermediate bar 98 includes a top surface 102, a bottom surface 106, and first sidewall 110 and second sidewall 114 located between the top surface 102 and bottom surface 106. However, as best seen in FIG. 19, one can see that the top surface 102 of the intermediate bar 98 is elevated relative to the first end 118 and second end 122 of the buckle 38. The elevated intermediate bar 98 provides a camming action against the outer sleeve 14 as will be described below.

In operation, and with reference to FIG. 19, the outer sleeve 14 is routed through the buckle 30 as generally shown by arrow A, wherein the first end 30 of the outer sleeve 14 is fed through the first port 126 from the bottom 123 to the top 124 of the buckle 38, over the elevated intermediate bar 98, and then through the second port 130 from the top 124 to the bottom 123 of the buckle 38. After the first end 30 has exited the second port 130 and been pulled to a desired tightness around the appendage, the hook and loop fastener on the outer surface 50 of the first end 30 of the outer sleeve 14 is mated with the hook and loop fastener on the outer surface 50 of the remainder of the outer sleeve 14 in order to mount the outer sleeve 14 around the appendage. Further, as the first end 30 of the outer sleeve 14 is being pulled from the second port 130, an input load 162 is applied generally perpendicularly to the top surface 102 of the elevated intermediate bar 98. The input load 162 causes the buckle to pivot per arrow 166 around the first lateral side 90 of the buckle 38, wherein the first lateral side 90 essentially acts as a fulcrum. As a result, an output load 170 is produced at the second lateral side 94 of the buckle 38 which forces the second lateral side 94 against the outer sleeve 14, thereby interlocking the outer surface 50 of the outer sleeve 14. It will be appreciated that as more of the outer sleeve 14 is pulled through the second port 130, the output load 170 applied to the outer sleeve 14 increases providing for a more sturdy arrangement. Thus, the elevated intermediate bar 98 provides an additional safety mechanism that prevents inadvertent disengagement of the first end 30 of the sleeve 14 from the buckle 38 when, for instance, a patient utilizing the tourniquet 10 is moved, dragged, etc. Those of ordinary skill in the art will recognize that the degree of elevation of the intermediate bar 98 relative to the first and second ends of the buckle can be modified so as to produce a desired output load applied to the outer sleeve 14.

Figure 20:
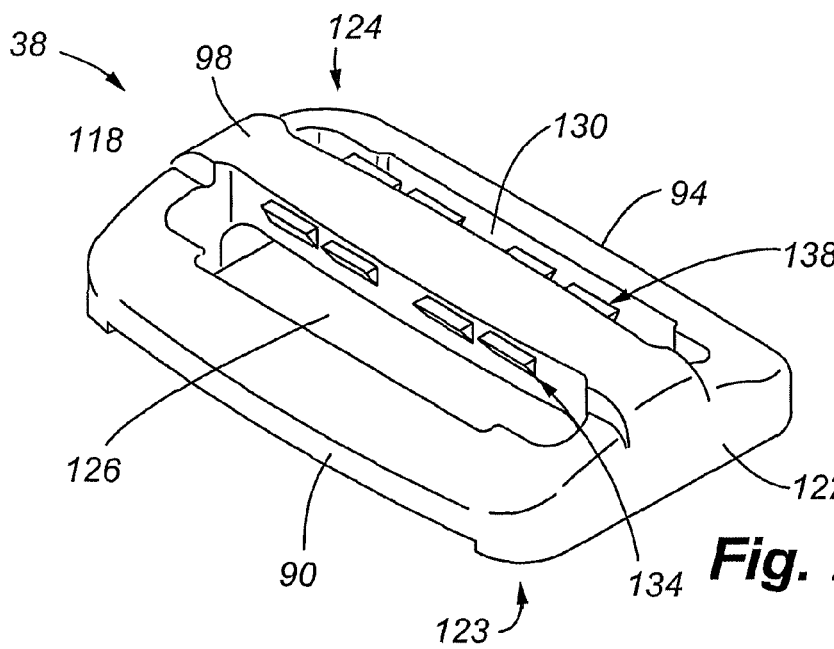
FIG. 20 is a perspective view of a buckle of the device according to another embodiment of the present invention with an elevated intermediate bar and first and second tooth sets.

Referring now to FIG. 20, another embodiment of the buckle 38 of the present invention is shown. More specifically, the buckle 38 includes an elevated intermediate bar 98 along with first tooth set 134 and second tooth set 138 situated adjacent the first port 126 and second port 130. In addition to the aforementioned camming action provided by the elevated intermediate bar 98 directed at the outer sleeve 14, the first tooth set 134 and second tooth set 138 increase the drag on the outer sleeve thus providing resistance to the free movement of the outer sleeve 14 relative to the buckle 38. As one will recognize, the combination of the elevated intermediate bar 98 and first tooth set 134 and second tooth set 138 provide extra safety mechanisms to further prevent inadvertent detachment of the first end 30 of the outer sleeve 14 from the buckle 38.

Figure 21:
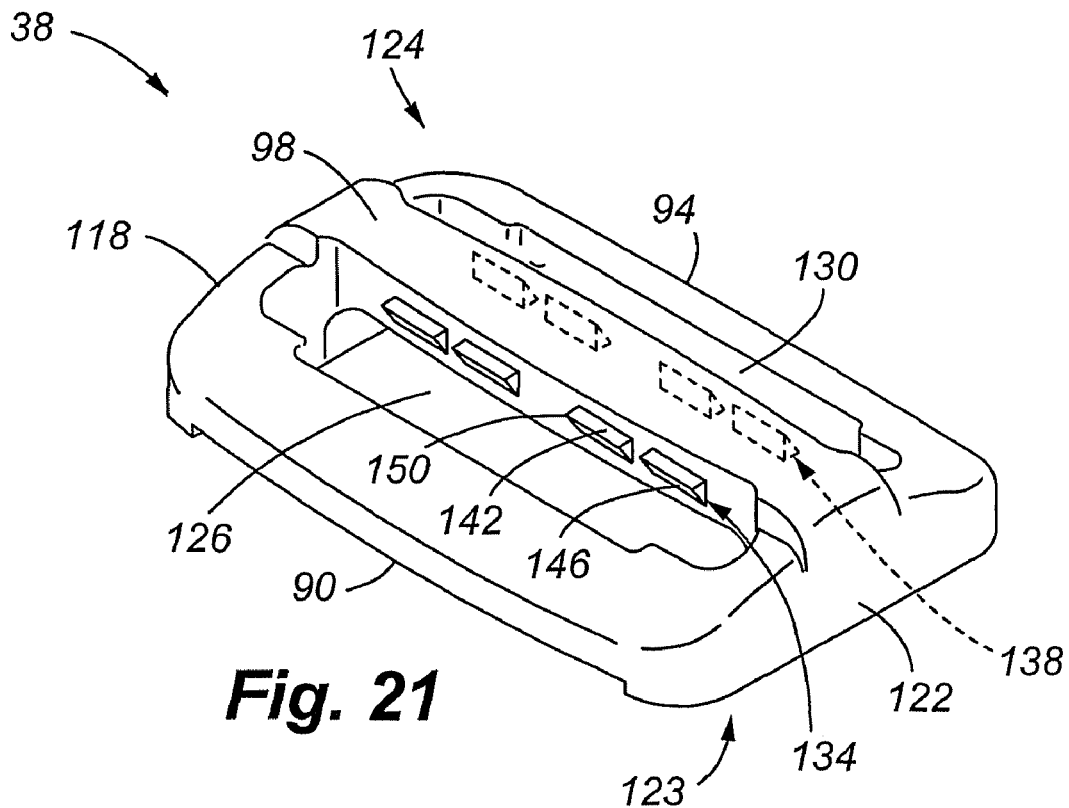
FIG. 21 is a perspective view of a buckle of the device according to another embodiment of the present invention with an elevated intermediate bar and a second tooth set inverted relative to a first tooth set.

With reference now to FIG. 21, a buckle 38 is provided similar to the buckle 38 of FIG. 20, but with the second tooth set 138 inverted. Such an arrangement allows the outer sleeve 14 to more freely slide through the buckle 38 during tightening movement of the outer sleeve due to the inclined surfaces 146 of the first tooth set 134 and second tooth set 138. However, loosening movement of the outer sleeve 14 relative to the buckle 38 is greatly inhibited due to the combination of the projections 150 of the second tooth set 138 interacting with the hook and loop fasteners of the outer sleeve 14 and the output load of the buckle 38 being applied against the outer sleeve 14.

Figure 22:
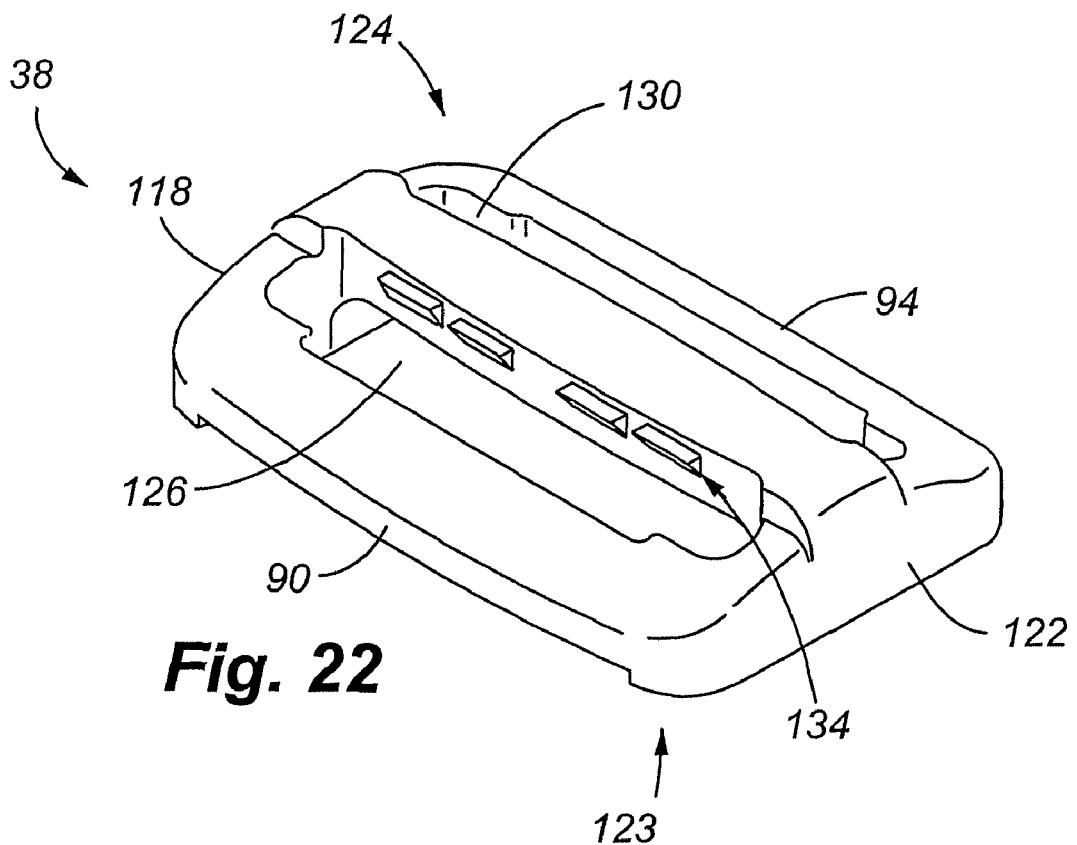
FIG. 22 is a perspective view of a buckle of the device according to another embodiment of the present invention with an elevated intermediate bar and only a single tooth set.

With reference now to FIG. 22, a buckle 38 is illustrated with an elevated intermediate bar 98 and only a first tooth set 134. As previously described, such an arrangement advantageously simplifies manufacturing of the buckle in addition to facilitating tightening and loosening movement of the outer sleeve 14 within the buckle 38.

Those of ordinary skill in the art will appreciate that other variations of the buckle 38 are within the scope of the present invention. For instance, while the first tooth set 134 of FIG. 22 is illustrated as being situated in the first port 126, ordinary artisans will appreciate that the first tooth set 134 can be situated in the second port 130, if desired. Additionally, it is contemplated that any of the aforementioned tooth sets could be inverted or not inverted so as to provide a desired amount of drag during loosening or tightening movement of the outer sleeve 14. Relevant considerations in determining which features to incorporate into a particular buckle 38 may include ease and cost of manufacturing, ease of assembly of the outer sleeve 14 and the buckle 38, the familiarity of the operators with the buckle 38, desired amount of drag applied to the outer sleeve 14, etc.

Further, while four teeth are shown in each tooth set in some of the above embodiments, it is contemplated that fewer teeth (including only a single tooth) may be provided to facilitate manufacturing, to provide for fewer sharp edges or for other reasons that an operator may desire. Additionally, more than four teeth may be provided to increase the gripping ability of the tooth set. Further, while each of the teeth is shown to be of a triangular profile, teeth of other shapes, are within the scope of the present invention such as bulbous-shaped teeth, teeth having only a single sharp point, teeth having two inclined surfaces, etc. Also, the angle of any inclined surfaces can be modified in order to provide more or less drag on the outer sleeve.

While the buckle of the present invention is preferably constructed of a polymer such as plastic or rubber, it is also contemplated that the buckle could be constructed of other materials such as metals, composites, etc.

The present invention has application for use in emergency medical situations for people. In addition, the invention also has application for use in veterinary medicine to apply a tourniquet to a body part or limb of an animal.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A tourniquet for restricting a flow of blood in a body part, the tourniquet comprising:
   (a) a first elongated member comprising:
      (i) a surface comprising both hook and loop structures;
      (ii) a first end and a second end; and
      (iii) a pocket;
   (b) a second elongated member positioned in the pocket, wherein a portion of the second elongated member is connected to the first end of the first elongated member;
   (c) a buckle connected to the second end of the first elongated member, the buckle comprising:
      (i) a first lateral side and a second lateral side; wherein the first and second lateral sides are spaced apart from and substantially parallel to each other;
      (ii) an intermediate bar located between the first and second lateral sides and substantially parallel to the first and second lateral sides, the intermediate bar including a top surface and a bottom surface with a first sidewall and a second sidewall therebetween;
      (iii) a first end and a second end interconnected to the first and second lateral sides and the intermediate bar;
      (iv) a first port located between the first lateral side and the intermediate bar;
      (v) a second port located between the second lateral side and the intermediate bar;
      (vi) a first tooth set situated on the first side wall of the intermediate bar and at least partially extending into the first port; and
      (vii) a second tooth set situated on the second side wall of the intermediate bar and at least partially extending into the second port;
      wherein the top surface of the intermediate bar is elevated with respect to the first and second ends of the buckle, with a first planar transition area between the top surface of the intermediate bar and the first end, and with a second planar transition area between the top surface of the intermediate bar and the second end, wherein the first and second planar transition areas are substantially parallel to the first lateral side;
      whereby the second end of the first elongated member is looped through the first port of the buckle to connect the first elongated member to the buckle;
      whereby the first end of the first elongated member is looped around the body part and through the first and second ports of the buckle so as to mount the first elongated member around the body part;
   (d) a windlass engaging the second elongated member, wherein the windlass is rotated to provide a tensile force in the second elongated member, wherein a compressive force is applied to the body part restricting the flow of blood in the body part; and
   (e) at least one hooked catch or a securing strap interconnected to the first elongated member for engaging a portion of the windlass and preventing a return rotation of the windlass after applying the tensile force.

2. A tourniquet for restricting a flow of blood in a body part, the tourniquet comprising:
   (a) an outer sleeve having first and second ends;
   (b) a buckle connected to the second end of the outer sleeve, the buckle comprising:
      (i) a top and a bottom;
      (ii) a first lateral side and a second lateral side, wherein the first and second lateral sides are spaced apart from each other;
      (iii) an intermediate bar located between the first and second lateral sides, the intermediate bar including a top surface and a bottom surface with a first sidewall and a second sidewall therebetween; and
      (iv) at least one first tooth situated on one of the first and second sidewalls of the intermediate bar, a first port located between the intermediate bar and the first lateral side of the buckle, wherein the at least one first tooth extends at least partially into the first port from the first sidewall of the intermediate bar, wherein:
   the at least one first tooth includes:
      a top surface that is substantially parallel to the top surface of the intermediate bar;
      an inclined surface; and
      a projection situated between the top surface of the at least one first tooth and the inclined surface;
      whereby the first end of the outer sleeve is looped around the body part and through the buckle so as to connect the outer sleeve around the body part;
      whereby the outer sleeve interacts with the at least one tooth to prevent the outer sleeve from disengaging from the buckle;
   (c) an inner strap in slidable engagement with the outer sleeve; and
   (d) a windlass connected to the inner strap;
   wherein a compressive force is applied to the body part upon applying a tensile force to the inner strap using the windlass, wherein the compressive force restricts the flow of blood in the body part.

3. The tourniquet of claim 2, wherein:
   the inclined surface of the at least one first tooth faces substantially toward the bottom of the buckle.

4. The tourniquet of claim 3, further comprising:
   a second port located between the intermediate bar and the second lateral side of the buckle, wherein at least one second tooth at least partially extends into the second port from the second sidewall of the intermediate bar; and
   wherein the at least one second tooth includes:
   a top surface that is generally parallel to the top surface of the intermediate bar;
   an inclined surface; and
   a projection situated between the top surface of the at least one second tooth and the inclined surface.

5. The tourniquet of claim 4, wherein:
   the inclined surface of the at least one second tooth faces substantially toward the bottom of the buckle.

6. The tourniquet of claim 4, wherein:
the inclined surface of the at least one second tooth faces substantially toward the top of the buckle.

7. The tourniquet of claim 2, wherein:
the inclined surface of the at least one first tooth generally faces substantially toward the top of the buckle.

8. The tourniquet of claim 2, further comprising:
a first end and a second end interconnecting the first and second lateral sides and the intermediate bar of the buckle;
wherein the top surface of the intermediate bar is elevated with respect to the first and second ends of the buckle.

9. A tourniquet for restricting a flow of blood in a body part, the tourniquet comprising:
(a) an outer sleeve having first and second ends;
(b) a buckle connected to the second end of the outer sleeve, the buckle comprising:
  (i) a top and a bottom;
  (ii) a first lateral side and a second lateral side, wherein the first and second lateral sides are spaced apart from each other;
  (iii) an intermediate bar located between the first and second sidewalls, the intermediate bar including a top surface and a bottom surface with a first sidewall and a second sidewall; and
  (iv) a first end and a second end interconnecting the first lateral side, the second lateral side, and the intermediate bar, wherein the top surface of the intermediate bar is elevated with respect to the first and second ends of the buckle with first elevation transition areas between the top surface of the intermediate bar and the first end, and with second elevation transition areas between the top surface of the intermediate bar and the second end;
  whereby the first end of the outer sleeve is looped around the body part and through the buckle so as to mount the first elongated member around the body part;
(c) an inner strap in slidable engagement with the outer sleeve; and
(d) a windlass connected to the inner strap;
wherein a compressive force is applied to the body part upon applying a tensile force to the inner strap using the windlass, wherein the compressive force restricts the flow of blood in the body part.

10. The tourniquet of claim 9, further comprising:
a first port located between the intermediate bar and the first lateral side of the buckle, wherein at least one first tooth at least partially extends into the first port from the first sidewall of the intermediate bar.

11. The tourniquet of claim 10, further comprising:
a second port located between the intermediate bar and the second lateral side of the buckle, wherein at least one second tooth at least partially extends into the second port from the second sidewall of the intermediate bar.

12. A method of restricting a flow of blood to a body part, the method comprising:
(a) wrapping a first elongated member having a buckle on a second portion thereof around the body part, the buckle having a first port and a second port with at least one tooth at least partially extending into each of the first and second ports;
(b) threading a first portion of the first elongated member through the first port in the buckle from the bottom to the top of the buckle;
(c) extending the first portion of the first elongated member over an intermediate bar of the buckle, wherein the buckle includes elevation transition areas between a top surface of the intermediate bar and directly adjacent first and second ends of the buckle;
(d) threading the first portion of the first elongated member through the second port in the buckle from the top of the buckle to the bottom of the buckle such that the at least one tooth in the first and second ports at least partially contact the first elongated member;
(e) detachably attaching the first portion of the elongated member to an outer surface of the elongated member so as to mount the first elongated member to the body part; and
(f) operating a tensioning mechanism operatively connected to a second elongated member slidably positioned relative to the first elongated member, wherein the tensioning mechanism develops a tensile force in the second elongated member, and wherein a compressive force is applied to the body part restricting the flow of blood in the body part.

* * * * *